United States Patent
Itoh et al.

(10) Patent No.: US 8,413,512 B2
(45) Date of Patent: Apr. 9, 2013

(54) METHOD FOR AGITATING LIQUEFIED MATERIAL USING QUARTZ CRYSTAL OSCILLATOR

(75) Inventors: Atsushi Itoh, Kanagawa (JP); Motoko Ichihashi, Kanagawa (JP)

(73) Assignee: ULVAC, Inc., Chigasaki-shi (JP)

( * ) Notice: Subject to any disclaimer, the term of this patent is extended or adjusted under 35 U.S.C. 154(b) by 0 days.

(21) Appl. No.: 12/515,312

(22) PCT Filed: Nov. 16, 2007

(86) PCT No.: PCT/JP2007/072318
§ 371 (c)(1),
(2), (4) Date: May 18, 2009

(87) PCT Pub. No.: WO2008/059970
PCT Pub. Date: May 22, 2008

(65) Prior Publication Data
US 2010/0054076 A1    Mar. 4, 2010

(30) Foreign Application Priority Data
Nov. 17, 2006 (JP) .................................. 2006-312253

(51) Int. Cl.
*G01N 29/00* (2006.01)
*G01G 3/16* (2006.01)
(52) U.S. Cl. ......... 73/590; 73/61.49; 73/61.79; 366/116
(58) Field of Classification Search ................. 73/54.41, 73/61.49, 61.79, 64.53, 590, 651; 366/116
See application file for complete search history.

(56) References Cited

U.S. PATENT DOCUMENTS

| | | | | |
|---|---|---|---|---|
| 3,925,734 A | * | 12/1975 | Smith | 331/41 |
| 4,513,620 A | * | 4/1985 | Uretsky et al. | 73/664 |
| 4,741,200 A | * | 5/1988 | Hammerle | 73/54.25 |
| 5,201,215 A | * | 4/1993 | Granstaff et al. | 73/54.41 |
| 5,527,460 A | * | 6/1996 | Trampler et al. | 210/198.1 |

(Continued)

FOREIGN PATENT DOCUMENTS

| | | |
|---|---|---|
| JP | 2002-310872 A1 | 10/2002 |
| JP | 2003-250515 | 9/2003 |

(Continued)

OTHER PUBLICATIONS

Partial Translation of JP2003-250515A, paragraphs [0031] to [0034], translated Oct. 28, 2011, 2 pages.*

(Continued)

*Primary Examiner* — Yogendra Gupta
*Assistant Examiner* — Emmanuel S Luk
(74) *Attorney, Agent, or Firm* — Kratz, Quintos & Hanson, LLP

(57) ABSTRACT

It is an object of the invention to provide an agitation method for sufficiently agitating a mixture of a solution such as a buffer solution and a material to be detected, with no need of any dedicated unit for agitation, for measurements using a quartz crystal oscillator. The method for agitating a liquefied material using a quartz crystal oscillator in vibrating the quartz crystal oscillator at a given frequency and measuring the variation of the frequency due to a substance in contact with the quartz crystal oscillator, is that the quartz crystal oscillator is vibrated at other frequency different from the given frequency and equal to or higher than the fundamental vibration frequency to agitate a liquid containing the substance.

4 Claims, 4 Drawing Sheets

U.S. PATENT DOCUMENTS

| | | | | |
|---|---|---|---|---|
| 5,698,931 | A * | 12/1997 | Shibata et al. | 310/338 |
| 5,796,506 | A * | 8/1998 | Tsai | 398/204 |
| 5,798,452 | A * | 8/1998 | Martin et al. | 73/32 R |
| 5,922,946 | A * | 7/1999 | Hirota et al. | 73/61.75 |
| 6,443,900 | B2 * | 9/2002 | Adachi et al. | 600/458 |
| 7,093,482 | B2 * | 8/2006 | Berndt | 73/61.75 |
| 7,331,232 | B2 * | 2/2008 | Itoh et al. | 73/590 |
| 7,570,125 | B2 * | 8/2009 | Ostanin et al. | 331/158 |
| 7,878,064 | B2 * | 2/2011 | Abbott et al. | 73/590 |
| 7,963,151 | B2 * | 6/2011 | Godfrey et al. | 73/64.56 |
| 2004/0005722 | A1 | 1/2004 | Takeuchi et al. | 436/518 |
| 2004/0092921 | A1 * | 5/2004 | Kadziauskas et al. | 606/27 |
| 2005/0069864 | A1 * | 3/2005 | Itoh et al. | 435/4 |
| 2009/0287205 | A1 * | 11/2009 | Ingle | 606/33 |

FOREIGN PATENT DOCUMENTS

| | | |
|---|---|---|
| JP | 2004-184258 A1 | 7/2004 |
| JP | 2005-98866 A1 | 4/2005 |
| JP | 2005-351799 A1 | 12/2005 |

OTHER PUBLICATIONS

Japanese Office Action dated Oct. 26, 2010 (in Japanese).
International Search Report for International Application No. PCT/JP2007/072318 dated Jan. 25, 2008.
Second Office Action issued Jan. 18, 2012 by the State Intellectual Property Office of the People's Republic of China in counterpart application No. 200780042452.4 with partial English translation (8 pages).

* cited by examiner

METHOD FOR AGITATING LIQUEFIED MATERIAL USING QUARTZ CRYSTAL OSCILLATOR

TECHNICAL FIELD

The present invention relates to a method for agitating a liquefied material for use in assaying a trace substance contained in the liquefied material.

BACKGROUND OF THE INVENTION

QCM (quartz crystal microbalance) is utilized for assaying interactions between biological substances such as DNA and proteins and for assays using antigen-antibody reactions.

Assaying with QCM is carried out by putting a buffer solution in contact with a quartz crystal oscillator electrode and adding a solution containing a sample as a subject to be assayed to the buffer solution, to measure the frequency variation occurring due to the binding of the sample to a substance immobilized on the quartz crystal oscillator electrode.

In that case, for example, the sample may happen to be precipitated on the bottom of the buffer solution or the sample may happen to float on the liquid surface so that the solution cannot be mixed together. Consequently, the solution cannot reach a constant final concentration, which causes inaccurate assays of the binding amount or causes no success in the binding rate analysis.

As one method for solving the problems, there is provided for example a method comprising placing an agitation rod in a container with a buffer solution injected therein and vibrating the solution therein along the upward and downward directions mechanically or rotating the solution (for example, patent reference 1).

Since a certain amount of the solution is needed so as to enable agitation of the solution by the method, however, the solution of a trace volume cannot be agitated sufficiently, disadvantageously. Because the solution cannot be agitated sufficiently, then, it is hard to carry out assays at high precision.

Due to the vibration of the quartz crystal oscillator with an electric power applied during assaying, furthermore, waves such as share wave and compressional wave generate. In case of an AT-cut quartz crystal oscillator of 27 MHz, share wave is reduced at a distance of about 100 nm from the surface of the quartz crystal oscillator, so that such wave cannot be used for agitation. It has been revealed experimentally that compressional wave itself cannot agitate liquefied materials.
Patent reference 1: JP-A-2002-310872

DISCLOSURE OF THE INVENTION

Problems that the Invention is to Solve

So as to solve the problems described above, it is an object of the invention to provide an agitation method for sufficiently agitating a mixture of a solution such as buffer solution and a material to be detected, with no need of any unit specified for agitation, for measurements using a quartz crystal oscillator.

Means for Solving the Problems

So as to solve the problems described above, the inventor made investigations to get the following findings.

According to a first aspect of the invention, the method for agitating a liquefied material using a quartz crystal oscillator is that in vibrating the quartz crystal oscillator at a given frequency and measuring the variation of the frequency due to a substance in contact with the quartz crystal oscillator, in accordance with the invention, the quartz crystal oscillator is vibrated at other frequency different from the given frequency and equal to or higher than the fundamental vibration frequency to agitate a liquid containing the substance.

According to a second aspect of the invention, the method for agitating a liquefied material of the first aspect of the invention is that the other frequency is the fundamental vibration frequency, the sub-vibration frequency or an Nth harmonic (N=3, 5, 7, . . . ) vibration frequency.

According to a third aspect of the invention, the method for agitating a liquefied material using a quartz crystal oscillator of the first or second aspect of the invention is that the quartz crystal oscillator is vibrated at a state fixed at the other frequency or a frequency sweeping within a range of ±100 kHz around the center of the other frequency, during the time of agitation.

According to a fourth aspect of the invention, still further, the method for agitating a liquefied material using a quartz crystal oscillator according to any one of the first to fourth aspects is that the electric power applied to the quartz crystal oscillator during the time of agitation is preset to 10-fold or more the electric power during the time of measurement.

According to a fifth aspect of the invention, the method for agitating a liquefied material using a quartz crystal oscillator according to any one of first to fourth aspects is that the quartz crystal oscillator is vibrated at an Nth harmonic (N=3, 5, 7, . . . ) vibration frequency during the time of measurement.

According to a sixth aspect of the invention, the method for agitating a liquefied material using a quartz crystal oscillator according to any one of first to fifth aspect is that the agitation is done before the measurement or the agitation is done between individual measurements when the measurement is continuously carried out.

Advantages of the Invention

According to the invention, no specific agitation unit is separately arranged during QCM measurement. Additionally, even a trace amount of a liquefied material for use in the measurement can be agitated. In accordance with the invention, still additionally, a liquefied material containing a trace amount of a sample can be agitated so sufficiently that measurement at a higher precision can be achieved.

DESCRIPTION OF SYMBOLS

Figure 1A:
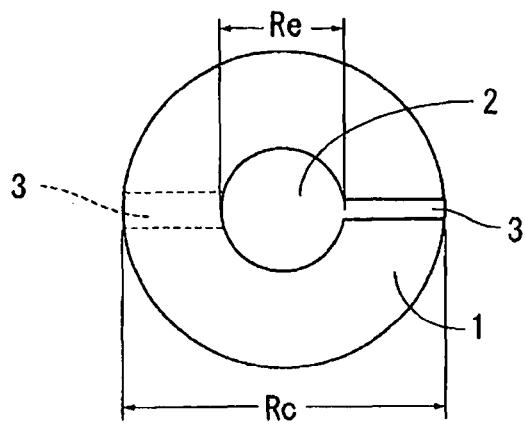
FIG. 1 Explanatory view of the construction of a quartz crystal oscillator (FIG. 1(a) is a plane view and FIG. 1(b) is a side view).

1. Quartz crystal plate
2. Electrode
3. Lead wire
4. Liquefied material
5. Container
6. Quartz crystal oscillator
7. π circuit
8. Network analyzer
9. RF generator
10. Personal computer
11. Frequency counter

BEST MODE FOR CARRYING OUT THE INVENTION

Any quartz crystal oscillators including quartz crystal oscillators for general use in QCM can be used with no specific limitation as the quartz crystal oscillator in accordance with the invention.

In accordance with the invention, agitation is done at other frequency different from a given frequency for use in measurement and equal to or higher than the fundamental vibration frequency of the quartz crystal oscillator. The other frequency is preferably the fundamental vibration frequency, the sub-vibration frequency or an Nth harmonic (overtone) (N=3, 5, 7, . . . ) vibration frequency. Using for example a quartz crystal oscillator of 27 MHz as the fundamental vibration frequency, the other frequency is preferably selected to be; 27 MHz or 135 MHz in case that the frequency for measurement is 81 MHz which is the 3rd harmonic frequency vibration frequency; and 81 MHz in case that 27 MHz is used as the frequency for measurement. Among the frequencies described above to enhance the agitation efficiency, the fundamental vibration frequency or the sub-vibration frequency is preferably selected.

The frequency for use in measurement may be the fundamental vibration frequency, however, an Nth harmonic vibration frequency which is less influenced by compressional wave is preferably used.

During agitation, preferably, the quartz crystal oscillator is continuously vibrated at any one of the frequencies or the quartz crystal oscillator is vibrated at a frequency sweeping within a range of ±100 kHz around the center of any one of the frequencies.

For measurement, the quartz crystal oscillator is applied with a load of an electric power of about 1 mW to oscillate and then the variation of the frequency is measured or the change of resonance frequency is measured by using a network analyzer or an impedance analyzer. Agitation is preferably carried out at an electric power ranging from 10- to 100-fold the electric power loaded on the quartz crystal oscillator during measurement. In case of the electric power, furthermore, the measured frequency may sometimes get unstable possibly involving a big noise, and therefore, it is preferable that agitation and measurement are done alternately or agitation is done before measurement.

The frequency may also be measured, using a network analyzer or an impedance analyzer or by a measurement method with a frequency counter during direct oscillation of the quartz crystal oscillator. During the use of a network analyzer, the frequency can be measured with or without use of π circuit. Quartz crystal oscillators for use in measurement and agitation may be set at not only one channel but also multi channels.

The invention will now be described specifically with reference to drawings.

Figure 1B:
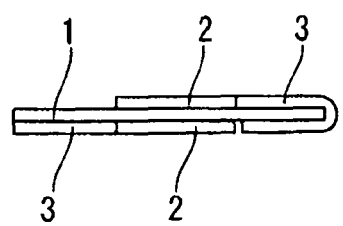

The quartz crystal oscillator for use in accordance with the invention includes, for example, a quartz crystal oscillator of the construction shown in FIG. 1. The quartz crystal oscillator is generally used for QCM, where counter electrodes 3, 3 are arranged on both the sides of a quartz crystal plate 1. For the 27-MHz specification, the quartz crystal plate 1 is about 60 µm in thickness and about 8.9 mm in diameter (Rc). The counter electrode 3 is made of, for example, gold and of a diameter (Re) of about 2.5 mm.

Figure 2:
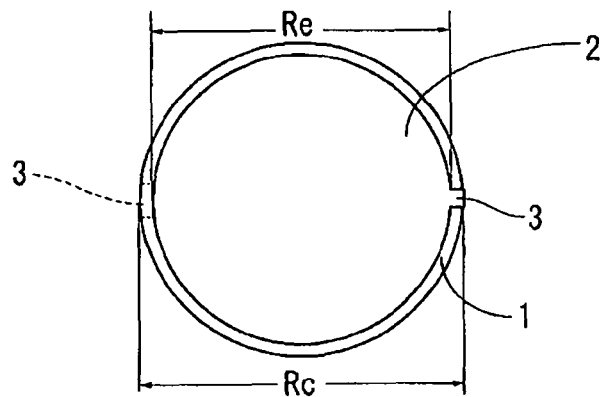
FIG. 2 Explanatory view of a quartz crystal oscillator in a preferable embodiment in one mode for carrying out the invention.

As shown in FIG. 2, more preferably, the diameter of the electrode 2 is about 8 mm, larger than the electrode of the general quartz crystal oscillator in the construction described above. The reason is that heat generated during agitation can be dispersed to suppress temperature increase of the quartz crystal oscillator and the solution, allowing the measurement at a lower noise. Herein, the electrode may be formed on any one or both of the surface and back faces.

Figure 3:
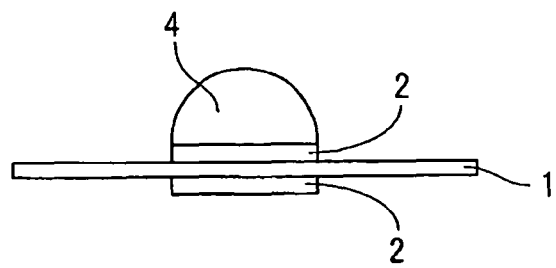
FIG. 3 Explanatory view of a liquefied material put in contact with the quartz crystal oscillator in one embodiment.
Figure 4:
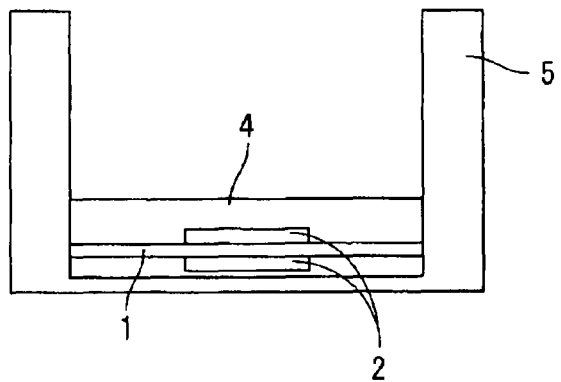
FIG. 4 Explanatory view of a liquefied material put in contact with the quartz crystal oscillator in another embodiment.
Figure 5:
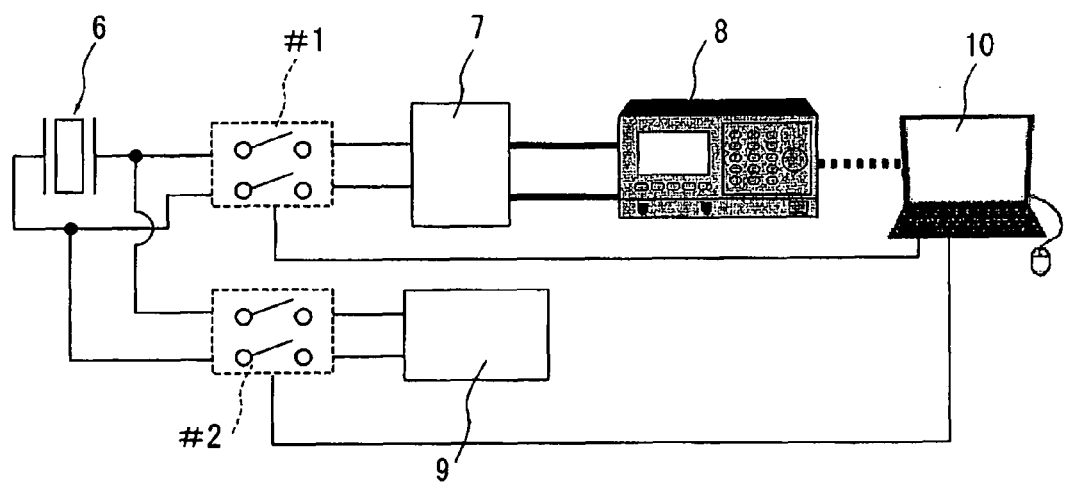
FIG. 5 View of the circuit composition of a biosensor apparatus for use in one Example of the invention.

So as to put a liquefied material in contact with the electrodes by using the quartz crystal oscillator, a method for arranging a solution 4 on the gold electrode 2 as shown in FIG. 3, a method for arranging the quartz crystal oscillator on the bottom of a container 5 and injecting a trace volume (about 500 µl or less) of the solution 4 above the quartz crystal oscillator as shown in FIG. 5, or a flow cell may be used but without any limitation.

EXAMPLE

One Example of the invention is now described.

In the present Example, measurement was carried out by arranging a solution on one electrode of the gold electrodes arranged on both the faces of the quartz crystal oscillator of the fundamental vibration frequency of 27 MHz, as shown in FIG. 3 so as to set the volume of a liquid as a handling subject to a trace volume.

The quartz crystal oscillator was connected to a circuit shown in FIG. 5.

The depicted circuit is composed of a circuit connecting the quartz crystal oscillator 6 through π circuit 7 to a network analyzer 8 and a circuit connecting the quartz crystal oscillator 6 to an RF generator 9. These circuits can freely be switched on and off with two relays #1 and #2. These relays #1 and #2 are controlled with a personal computer 10; in case that the relay #1 is closed, the quartz crystal oscillator oscillates for measurement; in case that the relay #2 is closed, the quartz crystal oscillator enforces agitation.

In case of carrying out the measurement with the quartz crystal oscillator 6, the quartz crystal oscillator was set to vibrate at a frequency around 81 MHz which is the 3rd harmonic frequency frequency; in case of enforcing agitation, the quartz crystal oscillator was set to vibrate at a frequency around the fundamental frequency (27 MHz) or around the sub-vibration frequency of the fundamental frequency of the fundamental wave (scanning within a range of ±100 kHz). The input electric power was 2 mW for the measurement and 200 mW for the agitation.

Figure 6:
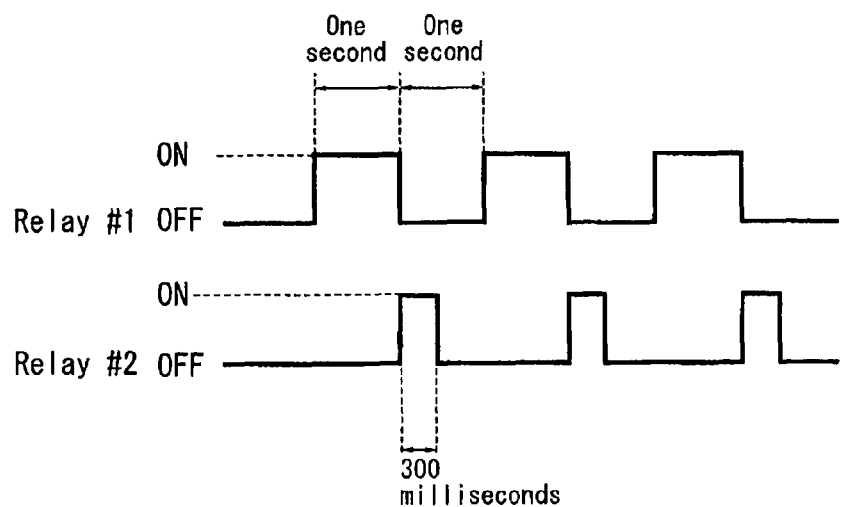
FIG. 6 Explanatory view of controlling relays #1 and #2 in the circuit.

As shown in FIG. 6, the relay #1 was controlled so as to repeat ON and OFF modes every one second, while the relay #2 was controlled so as to repeat taking ON mode for 300 milliseconds simultaneously with the start of the OFF mode of the relay #1 and then taking OFF mode thereafter.

Figure 8:
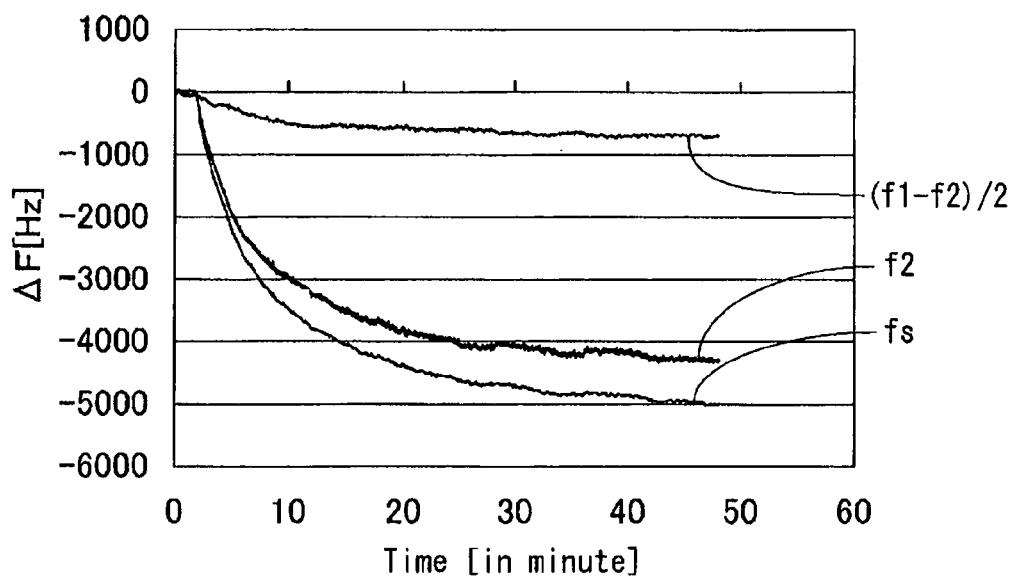
FIG. 8 Graphs showing the measurement results in one Example of the invention.
Figure 9:
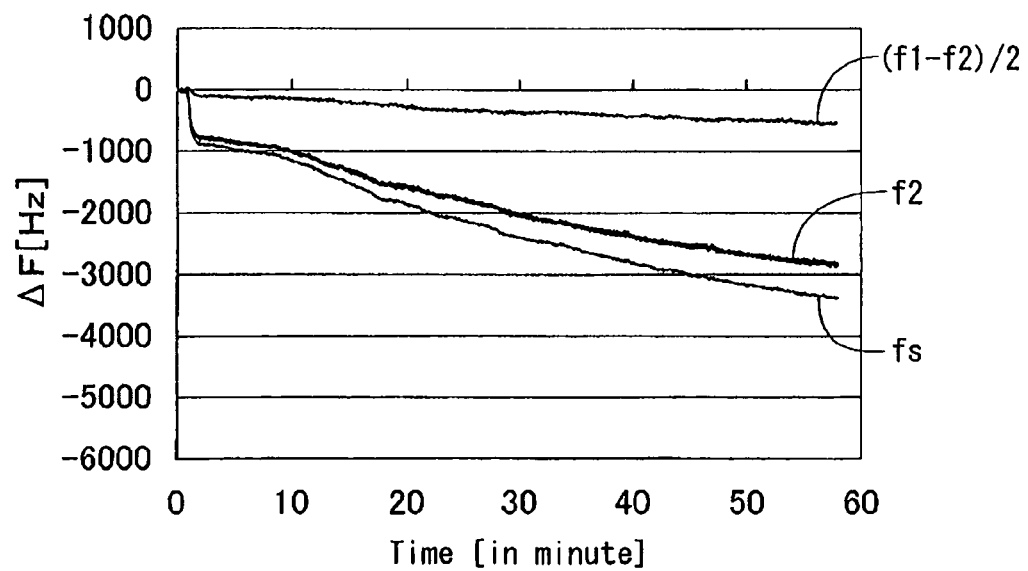
FIG. 9 Graphs showing the measurement results in Comparative Example.

Next, 9 µl of the buffer solution was placed on the gold electrode of the quartz crystal oscillator 6, and 1 µl of 0.1 mg/ml N-avidin was added FIGS. 8 and 9 show the measurement results with agitation under controls of the relays #1 and #2 and without agitation, respectively.

FIG. 8 shows that in the case with agitation, the variation of the frequency as measured after the N-avidin injection was on a gradually decreasing curve and the time required for the frequency to be stabilized was shorter compared with the case with no agitation. In the case with no agitation as shown in FIG. 9, in contrast, the frequency measured was decreased by −1000 Hz immediately after the N-avidin injection and then at a more or less leveled-off state and subsequently, decreased. This indicates that the frequency measured requires a time for stabilization in the case with no agitation.

The results show that agitation of a solution of as trace as several micro-liters level can be done with no dedicated agitation unit, enabling the analysis of the binding amount and the binding rate at a high precision.

Figure 7:
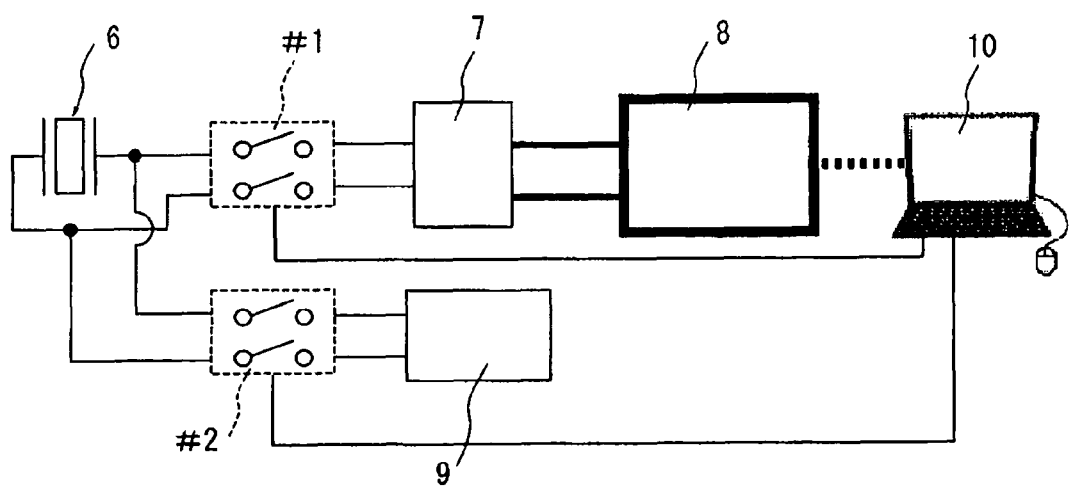
FIG. 7 View of a circuit composition depicting a variation example of the circuit composition in FIG. 5.

The circuit composition example described above is just an exemplification. Even a circuit using a frequency counter so as to oscillate the quartz crystal oscillator instead of the network analyzer as shown in FIG. 7 can also be used.

INDUSTRIAL APPLICABILITY

The invention can be utilized in a wide variety of fields for assaying interactions between biological substances such as DNA and proteins or assaying antigen-antibody reactions.

The invention claimed is:

1. A method for agitating a liquefied material using a quartz crystal oscillator in vibrating the quartz crystal oscillator at a given frequency and measuring the variation of the frequency due to a substance in contact with the quartz crystal oscillator, wherein the quartz crystal oscillator is vibrated at other frequency different from the given frequency and equal to or higher than the fundamental vibration frequency to agitate a liquid containing the substance, wherein the quartz crystal oscillator comprises a quartz crystal plate, a first electrode stacked on a side of the quartz crystal plate, and a second electrode stacked on a second side of the quartz crystal plate opposite from the first electrode, wherein the substance is in contact with the first electrode, wherein the liquid containing the substance is agitated at the fundamental vibration frequency or the sub-vibration frequency, and wherein the quartz crystal oscillator is vibrated at an Nth harmonic (N=3, 5, 7, ... ) vibration frequency during the time of measurement.

2. A method for agitating a liquefied material using a quartz crystal oscillator according to claim 1, wherein the quartz crystal oscillator is vibrated at the other frequency in a fixed way or vibrated at a frequency sweeping within a range of ±100 kHz around the center of the other frequency, during the time of agitation.

3. A method for agitating a liquefied material using a quartz crystal oscillator according to claim 1, wherein the electric power applied to the quartz crystal oscillator during the tune of agitation is set to 10-fold or more the electric power during the time of measurement.

4. A method for agitating a liquefied material using a quartz crystal oscillator according to claim 1, wherein the agitation is done before the measurement or the agitation is done between individual measurements when the measurement is continuously carried out.

* * * * *